United States Patent [19]

Rutledge

[11] 4,098,766

[45] Jul. 4, 1978

[54] METHOD OF OXIDATIVELY COUPLING ALKYL PHENOLS UTILIZING A TETRAVALENT MANGANESE-CARBON CATALYST

[75] Inventor: Thomas F. Rutledge, Wilmington, Del.

[73] Assignee: ICI Americas Inc., Wilmington, Del.

[21] Appl. No.: 787,507

[22] Filed: Apr. 14, 1977

[51] Int. Cl.² ............................................. C08G 65/44
[52] U.S. Cl. ................................ 528/217; 260/396 R; 260/396 N; 528/212
[58] Field of Search ............ 260/47 ET, 396 R, 396 N

[56] References Cited

U.S. PATENT DOCUMENTS

| 3,220,979 | 11/1965 | McNelis | 260/47 |
| 3,784,575 | 1/1974 | Rutledge | 260/396 R |
| 3,787,361 | 1/1974 | Nakashio et al. | 260/47 ET |
| 3,972,851 | 8/1976 | Olander | 260/47 ET |

*Primary Examiner*—Lester L. Lee
*Attorney, Agent, or Firm*—H. Jolyon Lammers

[57] ABSTRACT

Tetravalent manganese precipitated on porous carbon is useful to catalyze oxidative coupling reactions of alkyl phenols.

9 Claims, No Drawings

METHOD OF OXIDATIVELY COUPLING ALKYL PHENOLS UTILIZING A TETRAVALENT MANGANESE-CARBON CATALYST

DESCRIPTION OF THE PRIOR ART

Oxidation catalysts containing oxides of manganese are well known in the art. Catalysts containing oxides of manganese supported on granular alumina were disclosed in U.S. Pat. No. 1,995,274 assigned to Carbide and Carbon Chemicals Corporation. The oxidative coupling of phenols in the presence of a homogeneous catalyst containing manganese has also been known. For example U.S. Pat. No. 3,825,521 assigned to Asahi-Dow Ltd. suggests the coupling of 2,6-disubstituted phenols in the presence of chelate type catalyst comprising at least one divalent manganese salt and at least one selected diamino compound. U.S. Pat. No. 3,300,536 issued to McNelis and assigned to Sun Oil Company discloses a method of coupling 2-naphthol in the presence of a stoichiometric amount activated manganese dioxide. U.S. Pat. No. 3,787,361 assigned to Sumitomo Chemical Limited suggests a process for the production of polyphenylene oxide compounds by polymerizing phenols in the presence of a catalyst system composed of a manganese compound, a primary amine and an alcohol. A tetravalent manganese of carbon catalyst composition comprising 30 percent by weight manganese is disclosed by Louis A. Carpino in the Journal of Organic Chemistry, Vol. 35, No 11, (1970). None of the prior art however suggests a process for oxidatively coupling alkyl phenols in the presence of a hetrogeneous catalyst composition comprising 1–10 percent by weight of tetravalent manganese precipitated on porous carbon.

SUMMARY OF THE INVENTION

In accordance with the present invention there is provided a method of preparing a self condensation product from an alkylphenol in the presence of an oxygen-containing gas and a catalyst composition consisting essentially of about 1 to 10 percent by weight of tetravalent manganese precipitated on porous carbon.

In accordance with the present invention there is also provided a process of oxidative coupling 2,6-dialkyl-phenol to produce self-condensation products such as diphenoquinones and polyphenylene ethers which comprises contacting a solution of the phenol with oxygen or an oxygen containing gas in the presence of a hetrogeneous catalyst compositions consisting essentially of about 1 to 10 percent by weight of tetravalent manganese precipitated on porous carbon, optionally in the presence of an alkaline material and/or an amine.

DESCRIPTION OF THE INVENTION

The condensation-oxidation reaction products of alkylphenols prepared in accordance with the present invention can be categorized as either diphenoquinones or polyphenoxy ethers. The diphenoquinones are formed by carbon-carbon coupling of the alkyphenol in accordance with the following general reaction:

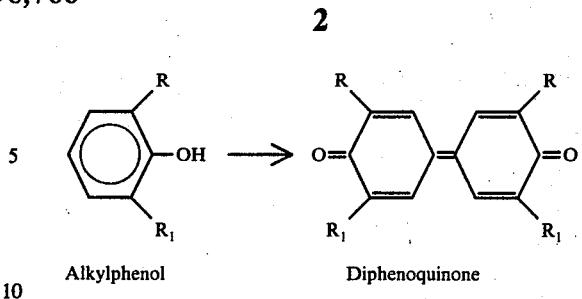

Alkylphenol → Diphenoquinone where R and $R_1$ are hydrogen, phenyl or alkyl groups containing preferably from 1 to 5 carbon atoms but wherein R and $R_1$ may not be both phenyl or hydrogen. Similarly, polyphenoxy ethers are prepared by carbon-oxygen coupling in accordance with the following general reaction:

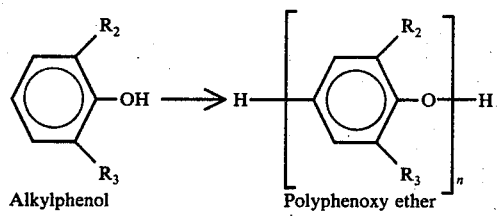

Alkylphenol → Polyphenoxy ether wherein $R_2$ is hydrogen, phenyl or an alkyl group of from 1 to 5 carbon atoms, $R_3$ is phenyl, an alkyl group of from 1 to 5 carbon atoms or hydrogen, but where $R_2$ and $R_3$ may not be both phenyl or hydrogen and wherein $n$ is an integer.

Alkylphenol

The alkylphenols which may be employed in carrying out the present invention include both the 2,6-dialkylphenols and the monoalkylphenols. When a 2,6-dialkylphenol is employed, either a diphenoquinone or a polyphenoxy ether may be prepared by the improved process of the present invention. The dialkylphenols useful in carrying out this invention include any alkylphenol haing alkyl groups of the above stated values in both the 2 and 6 positions, such as, for example 2,6-xylenol, 2-methyl-6-butylphenol, 2,6-diisobutylphenol, 2-octyl-6-methyl-phenol, 2-ethyl-6-methylphenol, 2,6-ditertiary-amylphenol, 2,6-ditertiary-butylphenol and 2-methyl-6-phenylphenol.

When a monoalkylphenol is employed, the improved process of the present invention tends to produce primarily polyphenoxy ethers having a low average molecular weight. As used herein, the term low molecular weight polyphenoxy ethers is intended to refer to those materials which have an average molecular weight of less than about 2,800 when prepared from a dialkylphenol and less than about 1,000 when prepared from a monoalkylphenol. Monoalkylphenols which may be employed in accordance with the present invention are the ortho-substituted phenols including, for example ortho-methyl-phenol, ortho-propylphenol, and ortho-tertiary-butylphenol.

The preferred monoalkyl and dialkyl phenols for use in the present invention are those having alkyl groups containing from 1 to about 5 carbon atoms.

Catalyst

The catalysts compositions useful in the present invention consist essentially of about 1 to 10 percent by weight of tetravalent manganese precipitated on porous carbon. The catalysts are unusually active and have a molecular oxygen consumption factor of at least 4.5 as determined by the molecular oxygen consumption test described hereinafter.

Carbons which are useful in the preparation of the catalysts have a surface area of at least 500 m²/grams and include those prepared from wood or wood products such as sawdust as well as from coconut shells, lignite, or coal. Catalysts prepared from lignite require an acid wash to substantially remove the sulfur and inorganic oxide impurities. In general the carbons that are suitable are those carbons which are prepared by pyrolysis, oxidation, steam extraction or acid extraction. Carbons such as most channel blacks possess a porosity and surface area insufficient for the purpose of this invention. Useful carbons are commercially available and include Darco G-60 activated carbon and similar carbons which are prepared from pin wood stumps, Darco KB activated carbon which is prepared from sawdust by a phosphoric acid process, Darco S-51 and Darco M activated carbons which are prepared from lignite by steam activation followed by an acid wash. It is highly desirable to remove any mineral impurities such as phosphates, sulphates or metal oxides from the carbon prior to using the carbon in the formation of the catalysts to avoid inter-reaction between the manganese component and these impurities. All Darco brand activated carbons are available from ICI United States Inc.

The tetravalent manganese/carbon catalyst having utility in the invention may be prepared by slurrying an aqueous permanganate salt solution such as potassium permanganate with a suitable carbon. In the case of sodium or potassium permanganate it has been observed that the purple color of the solution disappears during slurrying which indicates a valence reduction of the manganese $^{VII}$. Suitable permanganate salts include lithium permanganate, potassium permanganate, sodium permanganate, cesium permanganate and rubidium permanganate. Preferred permanganates are those which are substantially soluble in water. Less soluble permanganates salts which therefore would be less preferred include cesium permanganate and rubidium permanganate. After the permanganate solution has been slurried with the carbon the resulting catalyst is dried at temperatures below 25° C. and is then ready for use. It is highly desirable to dry the catalyst by vacuum drying or freeze drying as opposed to oven drying since high temperatures which prevail during oven drying tend to diminish the activity of the catalyst. For similar reasons it is suggested that the catalyst be kept in a cool dry environment prior to use. Catalyst kept at room temperature retain activity for approximately 2 months. Catalyst stored at lower temperatures retain activity for as long as 6 months.

The amount of manganese present in the total catalyst compositions may vary within the range of 1 to 10 percent by weight. For obvious economic reasons it is preferred to use as little manganese as possible. It has been discovered that a range of 1 to 10 percent of manganese precipitated on carbon provides a highly active catalyst. Percentages larger than 10 percent of manganese besides being economically disadvantageous also result in compositions having reduced activity. An optimum content of 2 to 7% manganese by weight of catalyst composition has been discovered to be most preferred for oxidative coupling of alkyl phenols. Catalyst containing less manganese component but within the suggested range require larger amounts of catalyst to achieve an optimum oxidative polymerization reaction.

The valence state of the active manganese component on the carbon must be four and this valence may be determined by utilizing a photoelectron spectrometer such as Model E S-200 available from AEI Scientific Apparatus Limited. Analyses of catalysts prepared for use in the process of the invention indicate that the active manganese is present only as tetravalent manganese. Total manganese content may be determined by atomic absorption analysis.

Solvent

In carrying out the process of the present invention, the alkylphenol is first dissolved in a suitable solvent. Representative organic solvents in which the alkylphenols may be dissolved are the aromatic hydrocarbons, including benzene, toluene, ethylbenzene, xylene, mesitylene, and the like; the nitrated aromatic hydrocarbons, including nitrobenzene, dinitrobenzene, nitrotoluene, chlorinated aromatic hydrocarbons and the like; alicyclic hydrocarbons, including cycloheptane, cyclohexane, and the like; tertiary-butyl alcohol; tertiary-amyl alcohol; dimethylformamide; dimethylsulfoxide; dioxane; ketones; and esters of lower aliphatic acids. Of these, it is especially preferred to employ aromatic hydrocarbons.

The amount of solvent employed has not been found to be narrowly critical to the preparation of self-condensation products in accordance with the present invention. However, the amount of solvent employed should be sufficient to dissolve the alkylphenol being reacted. For most solvent-alkylphenol mixtures, about 2 ml. of solvent per gram of alkylphenol is sufficient to dissolve the phenol.

When a diphenoquinone is prepared, water may also be included as an additional solvent in the reaction mixture. In this case, preferred results have been achieved when from about 200 ml. to about 1,400 ml. of water are added per liter of organic solvent. If either less than or more than this amount of water is utilized, optimum yields of diphenoquinone are not generally achieved.

When polyphenoxy ethers are prepared in accordance with the present invention, it has been found that the use of an excess of solvent or the addition of water to the reaction mixture tends to produce ethers of relatively low molecular weights. Thus, if it is desired to produce a product having the highest possible molecular weight, only the minimum amount of solvent and no water should be included in the reaction mixture. The actual amount of solvent, in this situation, may vary depending upon the alkylphenol employed, type of stirring, etc.

Optional Alkaline Material

In accordance with the present invention, it has been found that satisfactory products can be produced utilizing less catalyst or, when the same amount of catalyst is employed, the yield of product can be improved, by also including an alkaline material in the reaction mixture. The alkaline material useful in achieving the improved results of the present invention is selected from the group consisting of alkali metal hydroxides and alkali metal carbonates. The alkaline material may be added either as a single compound or as a mixture of compounds.

When it is desired to produce diphenoquinones, any of the above-mentioned alkaline materials may be utilized. In producing the diphenoquinones, it has been found that to produce optimum results the amount of alkaline material should be equal to about 1 to 10 moles based on 100 moles of alkylphenol employed. Either more than or less than this amount of alkaline material may be included in the reaction mixture if desired. However, the use of more alkaline material has not been found to significantly increase the yield of diphenoquinone and it is, therefore, not generally desirable to include additional material in the reaction mixture. Also, although some diphenoquinone is produced when less alkaline material is utilized, this is generally not desirable.

In preparing polyphenoxy ethers in accordance with the present invention, a distinction must be drawn depending upon whether the desired product is the low molecular weight polyphenoxy ether, referred to above, or whether other polyphenoxy ethers are desired. If low molecular weight polyphenoxy ethers are desired, either an alkali metal hydroxide or an alkali metal carbonate may be added to the reaction mixture. However, if it is desired to produce polyphenoxy ethers or a higher average molecular weight, only an alkali metal hydroxide should be utilized. Here also, the amount of alkaline material has not been found to be narrowly critical to the production of products in accordance with the present invention. However, the amount of alkaline material required to produce optimum yields is generally equal to or greater than that required to produce the optimum yield of diphenoquinone. It has been found that, in most instances, an amount of alkaline material equal to about 3 to 25 mole based on 100 moles of alkylphenol present in the reaction mixture will produce an optimum yield of the polyphenoxy ether. As in the case of the diphenoquinones, either less than, or more than, this amount may also be utilized. However, especially in those cases when no water is included in the reaction mixture; i.e., when high molecular weight products are desired, an excessive amount of alkaline material should not be utilized. If too much alkaline material is utilized in these situations, mechanical problems such as stirring, etc., may be encountered. The alkaline material may be added to the reaction mixture either alone or combined with the catalyst.

Optional Amine Component

The amine component is not critical to the invention and may be any of the following compounds or mixtures thereof:

Cyclic aromatic amines, such as pyridines, substituted alkyl pyridines and quinolines.

Cyclic saturated amines, such as piperazines and N-alkyl piperazines,

Aliphatic mono amines, such as n-butylamine, di-n-butylamine,

Aliphatic diamines such as tetramethylethylenediamine (TMEDA) or dimethylethylenediamine.

Both the optional amine and alkaline material tend to increase the molecular weight of polyphenylene ethers as well as increase the rate of the reaction.

The effective amount of the optional amine component may generally range from 1 to 50 moles per 200 moles of phenol oxidized: this range is based on the presence of approximately 0.25 g. of tetravalent manganese in the catalyst used. Variations in the amount of manganese IV present will affect the optimum amount of amine.

The reaction mixture comprising alkylphenol, solvent, catalyst, and optional alkaline material and amine is contacted with a suitable oxidizing agent to convert the alkylphenol to the desired product. Oxidizing agents which may be employed in carrying out the present invention include oxygen either alone or as an oxygen-containing gas, such as air. The oxygen may be introduced into the reaction mixture either directly as oxygen gas or as an oxygen-generating material such as ozone, hydrogen peroxide, or an organic peroxide. The amount of oxygen utilized should be sufficient to convert all of the alkylphenol to the desired product. To assure that sufficient oxygen is present, oxygen should be introduced into the reaction mixture continuously during the course of the reaction.

The reaction conditions employed may be varied depending upon the product desired. While the formation of diphenoquinones is favored when the reaction mixture is heated to a temperature in the range of from about 40° C. to about 70° C., diphenoquinones may not be the most desirable product. When it is desired to produce primarily the polyphenoxy ethers, the reaction is preferably conducted at a lower temperature, generally in the range of from about 10° C. to about 30° C. It has been found that the higher molecular weight products are best produced at lower temperatures and that raising the reaction temperature tends to lower the molecular weight of the resulting polyphenoxy ethers. Temperatures other than those mentioned above may be employed. However, conversion to the desired product is generally reduced if the reaction is conducted at such temperatures. The amount of time required for completion of the reaction depends on the temperature employed and the other variables such as the concentration of alkylphenol, the amount of catalyst, and the amount of alkaline material and amine employed. However, it has been found that, in general, the reaction is completed in 6 hours or less.

As will be appreciated by those skilled in the art, the process of the present invention frequently results in the production of a mixture of products. Thus, when a diphenoquinone is produced, there may also be included in the product some low molecular weight polyphenoxy ethers. These latter products may be separated and the diphenoquinone purified by procedures which are now well known in the art. These procedures generally take advantage of the fact that the diphenoquinone is insoluble in materials in which the low molecular weight product will dissolve easily. Similary, when polyphenoxy ethers are prepared, there may result a mixture of products having a variety of average molecular weights. These may also be separated, if desired, as is known to those skilled in the art. This also is done by taking advantage of the relative solubility and insolubility of the several fractions. The catalyst may be removed from the products by similar techniques well known in the art.

The following procedure is representative of those which may be utilized to isolate and separate the products produced in accordance with the present invention.

If a solvent such as an aromatic hydrocarbon is employed, the diphenoquinone will precipitate during the course of the reaction. The solids are filtered from the reaction mixture and washed with an organic solvent such as xylene to remove any unreacted alkylphenol or low molecular weight polyphenoxy ether. The solid diphenoquinone is then separated from the catalyst by extracting with a suitable solvent, such as methylene chloride, followed by evaporation of the solvent. The lower molecular weight polyphenoxy ethers are soluble in aromatic hydrocarbons and may be precipitated therefrom by the addition of methanol or acetone. The higher molecular weight polyphenoxy ethers are soluble in, for example, trichloro ethylene and chloroform and may be precipitated by the addition of a second solvent in which they are insoluble such as acetone or methanol.

If desired, the diphenoquinone/catalyst mixture may be hydrogenated directly to produce the corresponding biphenol. In such a case, the diphenoquinone/catalyst mixture can be removed from the reaction mixture by filtration, slurried in a suitable solvent such as methanol, and hydrogen may be introduced at an elevated temperature until the red color of the diphenoquinone disappeared. A hydrogenation catalyst such as Raney nickel or palladium-carbon may be added to accelerate the hydrogenation reaction.

In order to described the present invention so that it may be more clearly understood, the following examples are set forth. These examples are given primarily for the purpose of illustration and any enumeration of detail contained therein should not be interpreted as a limitation on the concept of the present invention.

MOLECULAR OXYGEN CONSUMPTION FACTOR (MOCF)

The MOCF represents the amount of oxygen consumed in 2 hours in an oxidation reaction under specified conditions. The amount is expressed in millimoles of molecular oxygen. The conditions are as follows; a 50 ml flask held in a semi-automatic shaker apparatus is charged with:

2.44 grams (20 mmoles) 99.9% pure 2,6-xylenol,
20 ml of commercial grade tert-amyl alcohol
0.10 grams of 85% powdered potassium hydroxide, and an amount of catalyst representing 0.025 grams of tetravalent manganese.
The reaction mixture is heated to 50° C. and allowed to consume oxygen at atmospheric pressure as required from a calibrated gas buret filled with oxygen. The amount of oxygen consumed in 2 hours is measured and represents the MOCF.

Catalyst Preparation

EXAMPLE 1

To 40 g of Darco G-60 Special activated carbon suspended in 400 ml of water was added over a 10 minute period 6.4 g of $KMnO_4$ dissolved in 200 ml of water. After 1 hour stirring at room temperature the color of $KMnO_4$ had disappeared and the pH of the reaction liquid was determined to be between 9–10 by pH test paper. After filtration and washing with 300 ml of water the material was dried in a vacuum oven for 2 hours at 40°–150° C. The catalyst contained 5.2% tetravalent manganese.

EXAMPLE 2

The procedure of example 1 was repeated using 1.3 g of $KMnO_4$. The catalyst contained 1% tetravalent manganese.

EXAMPLE 3

The procedure of example 2 was repeated using 3.2 g of $KMnO_4$. The catalyst contained 2.5% tetravalent manganese.

EXAMPLE 4

The procedure of example 1 was repeated using 12.8 g of $KMnO_4$. The catalyst contained 10% tetravalent manganese.

EXAMPLE 5

The procedure of example 1 was repeated but the material was "freeze dried" in a vacuum oven at room temperature.

EXAMPLE 6

The procedure of example 5 was repeated using 40 g of Darco KB Special activated carbon. The catalyst contained 5% tetravalent manganese.

EXAMPLE 7

The procedure of example 5 was repeated using 40 g of Darco S-51 activated carbon. The catalyst contained 5% tetravalent manganese.

EXAMPLE 8

The procedure of example 1 was repeated using Darco-M activated carbon. The catalyst contained 5% tetravalent manganese.

Process

EXAMPLE 9

A 500 ml reactor kettle equipped with stirrer, $N_2$ sparge system and oxygen inlet was charged with 65 ml of toluene and 0.75 ml of pyridine (9 mmole). After stirring under a nitrogen atmosphere 0.20 g of powdered 85% KoH was added followed by 24.4g of 99.9% 2,6-xylenol (200 mmol) and 15 ml of toluene. The mixture was stirred for 15 minutes after which 2.5g of a 5% manganese $^{IV}$ catalyst prepared according to Example 5 and 20 ml of toluene was added. The mixture was stirred for an additional half hour and then both stirrer and nitrogen were turned off. The reactor was flushed for ¼ hour at 20° with oxygen and then sealed. Oxygen supply was continued, the temperature allowed to rise up to 26°–30° and the mixture was stirred for the next 6 hours. The oxygen consumption was 95.5 mmoles of which 95 mmoles was consumed during the first 4 hours. After turning off the stirrer the reaction mixture was allowed to stand.

The viscous black product was diluted with 150 ml toluene, stirred and centrifuged. The clear yellow viscous toluene was decanted. The residue was stirred with 200 ml toluene, and centrifuged. The toluene solution was mixed with the original toluene centrifugate, evaporated to 150 ml, and poured into 400 ml stirred acetone. The resulting polymer weighed 4.8 grams (20 mole % yield). It melted 230°–260°. Gel permeation chromatography showed $\overline{Mn}$ = 17,800; $\overline{Mw}$ = 89,600; and polydispersity = 5.04.

The toluene-acetone solution was evaporated to dryness. The reddish yellow polymer weighed 1.6 gram and was low molecular weight oligomer of 2,6-xylenol (6.6% yield).

The catalyst-polymer solid residue from the toluene washes was air dried. The solid was stirred with 300 ml methylene chloride, centrifuged, and the methylene chloride solution was filtered through a thin pre-coat of Super-Cel filter aid. This operation was repeated once. The filtered methylene chloride solution was allowed to stand to precipitate the polymer-methylene chloride complex. The complex was removed by filtration. The methylene chloride was evaporated to dryness to yield 2.0 grams of red tetramethyldiphenoquinone (8.4 mole % yield).

The solid catalyst remaining after the methylene chloride extractions was stirred with 300 ml 1,1,2-trichloroethylene and centrifuged. This operation was repeated once. The polymer-methylene chloride complex was dissolved in the trichloroethylene centrifugate, and the solution filtered through Super-Cel filter aid. The filtrate was evaporated to 550 ml, and then dropped into 1900 ml stirred acetone. The precipitated polymer was removed by filtration, and was washed once with acetone. The polymer was dried at 60°. The dried polymer was white, and weighed 14.7 grams (61.5 mole % yield). The polymer softened at 250°, and was still only soft at 300°. GPC analysis showed $\overline{M}n$ = 30,900; $\overline{M}w$ = 156,000; polydispersity = 5.07. Total yield of high polymer was 81.5 mole % with average $\overline{M}n$ = 27,700.

Example 9–23 illustrates the activity of the catalysts and the method of oxidative coupling of alkyl phenols. The Examples 10–23 were all conducted according to the procedure of Example 9 varying as indicated in the Table the amounts of alkaline material and the amounts and types of amine. Mixing orders were varied as indicated. All molecular weights were determined by gel permeation chromatography (GPC).

The high Mw polymers were cast into films by the following technique. The polymer was dissolved in trichlorethylene and the solution was cast on a lecithin coated glass plate using a standard doctor blade. For 1 mil film, a 10% solution of polymer was cast using a 10 mil setting on the doctor blade. Solvent was allowed to evaporate overnight, and the film was peeled from the plate. The film was dried for at least one week at room temperature before tensile strength was determined. Drying can be accelerated by placing the films in a forced air oven at 60°–125° C. Tensile strength data as indicated in the table was obtained according to ASTM D-882.

TABLE

| Example | Catalyst Amt. | Method (D) | Other | Mix Order | Mole % to Conv. to Low $M_W$ | Mole % to Conv. to Med. $M_W$ | Mole % to Conv. to High $M_W$ | GPC Mn Med. $M_W$ | GPC Mn High $M_W$ | Cast Films Tensile Strength High $M_W$ |
|---|---|---|---|---|---|---|---|---|---|---|
| 9 | 5 | 1 | Ethanolamine | (A) | 9.5 | 35.8 | 21.6 | — | — | |
| 10 | " | " | TMEDA (G) | " | 8 | 54.6 | 4 | 10,000 | — | |
| 11 | " | " | " | " | 9.2 | 22 | 46 | — | 21,400 | 7,100 |
| 12 | " | " | Pyridine | " | — | 5 | 38 (a) (H) 41.6(b) | — | (a)9,680 (b)44,500 | (a)6,700 (b)7,700 |
| 13 | " | " | None | (B) | 15.8 | 54.2 | 0 | — | — | |
| 14 | " | " | Pyridine | (A) | 6.3 | — | (a)25.8 (b)35.0 | — | (a)19,200 (b)21,800 | |
| 15 | " | " | "(F) | (C) | 5.8 | — | (a)27.6 (b)46 | — | (a)20,000 (b)39,400 | |
| 16 | 1.25 | 4 | " | (C) | 35.8 | 0 | 7 | — | — | |
| 17 | 2.5 | 1 | " | " | 20.6 | — | 17 | — | — | |
| 18 | 2.5 | 6 | " | (A) | — | — | (a)16.6 (b)64 | — | (a)16,500 (b)33,900 | |
| 19 | 2.5 | 7 | " | " | 5 | — | (a)28.8 (b)51.4 | — | (a)13,600 (b)22,900 | |
| 20 | 2.5 | " | (F) | (C) | — | — | (a)17.1 (b)59.5 | — | (a)11,711 (b)29,100 | |
| 21 | 2.5 | " | 2-Picoline | (A) | 21 | 0 | 57.6 | — | 7,060 | |
| 22 | 2.5g | 8 | Pyridine | (C) | — | — | (a)52.5 (b)7.1 | — | (a)11,600 (b)18,700 | |
| 23 | " | " | " | " | — | — | (a)42 (b)41.6 | — | (a)20,400 (b)38,600 | 7,400 |

(A) Toluene and amine stirred, KOH added, then 2,6-xylenol added under $N_2$. Stirred ¼ hour under $N_2$. Catalyst added, rinsed in with toluene. Stirred ¼ hour, $N_2$. Stirrer off, flush with oxygen for ¼ hour, 25°. Then on stirrer.
(B) Same as (A), except amine omitted.
(C) Toluene and KOH stirred, 2,6-xylenol added. Stirred ¼ hour, $N_2$. Catalyst stirred in 10 toluene, amine added, stirred occasionally for ¼ hour. Catalyst-amine slurry added to toluene-KOH-2,6-xylenol. Stirred ¼ hour, $N_2$. Then stirrer off, flushed with $O_2$ ¼ hour, 25°. Then on stirrer.
(D) Method indicates that the catalyst was prepared by the numbered example.
(F) Pyridine pre-mixed with catalyst in toluene instead of adding amine to toluene-KOH-2,6-xylenol as in some previous runs.
(G) TMEDA - Tetramethylethylene diamine.
(H) (a)indicates fraction extracted by toluene and precipitated into acetone.
(b)indicates higher MW fraction extracted by methylene chloride and precipitated into acetone.

What is claimed is:

1. A method of preparing a self condensation product from an alkyl phenol which comprises contacting a solution of the alkyl phenol with oxygen or an oxygen containing gas in the presence of a heterogeneous catalyst composition consisting essentially of about 1 to 10 percent by weight of tetravalent manganese precipitated on porous carbon, which is substantially free of mineral impurities.

2. A method as claimed in claim 1 wherein the alkylphenol is additionally contacted with an alkaline solution.

3. A method as claimed in claim 2 wherein the alkylphenol is additionally contacted with an amine.

4. A method as claimed in claim 1 wherein the alkylphenol is 2,6-dialkylphenol.

5. A method as claimed in claim 1 wherein the alkylphenol is 2,6-xylenol.

6. A method as claimed in claim 1 wherein the alkylphenol is 2,6-ditertiarybutyl phenol and the condensation product is substantially diphenoquinone.

7. A method as claimed in claim 1 wherein the alkylphenol is 2-methyl-6-phenyl phenol and wherein the condensation product is polyphenylene ether.

8. A method as claimed in claim 1 wherein the catalyst composition contains about 2 to 7% by weight of tetravalent manganese.

9. A method as claimed in claim 1 wherein the catalyst composition contains about 5% by weight of tetravalent manganese.

* * * * *

UNITED STATES PATENT AND TRADEMARK OFFICE
CERTIFICATE OF CORRECTION

PATENT NO. : 4,098,766
DATED : July 4, 1978
INVENTOR(S) : Thomas F. Rutledge

It is certified that error appears in the above-identified patent and that said Letters Patent are hereby corrected as shown below:

Column 8, Line 59, "4,8 grams" should read --4.8 grams--.

Signed and Sealed this

Sixteenth Day of January 1979

[SEAL]

Attest:

RUTH C. MASON
Attesting Officer

DONALD W. BANNER
Commissioner of Patents and Trademarks